United States Patent
Furuta (10) Patent No.: US 9,445,770 B2
(45) Date of Patent: Sep. 20, 2016

(54) NUCLEAR MEDICINE DIAGNOSTIC APPARATUS

(75) Inventor: Masafumi Furuta, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 107 days.

(21) Appl. No.: 14/232,812

(22) PCT Filed: Jul. 28, 2011

(86) PCT No.: PCT/JP2011/004297
§ 371 (c)(1),
(2), (4) Date: Jan. 14, 2014

(87) PCT Pub. No.: WO2013/014715
PCT Pub. Date: Jan. 31, 2013

(65) Prior Publication Data
US 2014/0128729 A1    May 8, 2014

(51) Int. Cl.
*A61B 6/00* (2006.01)
*A61B 6/04* (2006.01)
*A61B 6/03* (2006.01)

(52) U.S. Cl.
CPC ............ *A61B 6/0435* (2013.01); *A61B 6/037* (2013.01); *A61B 6/0414* (2013.01); *A61B 6/502* (2013.01)

(58) Field of Classification Search
CPC .. A61B 6/037; A61B 6/0414; A61B 6/0435; A61B 6/502
See application file for complete search history.

(56) References Cited

U.S. PATENT DOCUMENTS

| 4,837,881 | A | * | 6/1989 | Kondo et al. | 5/653 |
| 4,951,334 | A | * | 8/1990 | Maier | 5/653 |
| 5,134,735 | A | * | 8/1992 | Rose | 5/730 |
| 7,849,540 | B2 | * | 12/2010 | Hill | 5/632 |
| 8,483,354 | B1 | * | 7/2013 | Kosnitsky et al. | 378/37 |
| 2004/0039428 | A1 | * | 2/2004 | Williams et al. | 607/91 |

FOREIGN PATENT DOCUMENTS

| JP | 2008-232913 A | 10/2008 |
| JP | 2009-189726 A | 8/2009 |
| JP | 2009-300319 A | 12/2009 |

OTHER PUBLICATIONS

International Search Report, w/ English translation thereof, issued in International Application No. PCT/JP2011/004297 dated Aug. 30, 2011.

* cited by examiner

*Primary Examiner* — Ruth S Smith
(74) *Attorney, Agent, or Firm* — McDermott Will & Emery LLP (57) ABSTRACT

A nuclear medicine diagnostic apparatus includes a support unit for supporting an inspection object from front, an opening for receiving a breast of the inspection object supported by the support unit, a detector ring opposed to the inspection object across a supporting surface of the support unit for detecting radiation generated from the breast, a chest mat provided around the opening formed in the support unit for supporting the chest of the inspection object, and an outer mat provided outward of the chest mat for supporting the inspection object. The chest mat is formed of a material having a greater sagging rate than the outer mat.

9 Claims, 10 Drawing Sheets

NUCLEAR MEDICINE DIAGNOSTIC APPARATUS

RELATED APPLICATIONS

This application is the U.S. National Phase application under 35 U.S.C. §371, of international Application No. PCT/JP2011/004297 filed on Jul. 28, 2011, the disclosure of which Application is incorporated by reference herein.

TECHNICAL FIELD

This invention relates to a nuclear medicine diagnostic apparatus for obtaining nuclear medical data of an inspection object based on radiation (e.g. gamma rays) generated from the inspection object medicated with a radioactive drug.

BACKGROUND ART

Conventionally, there is a PET (Positron Emission Tomography) apparatus as this type of nuclear medicine diagnostic apparatus, i.e. ECT (Emission Computed Tomography). The PET apparatus is constructed to reconstruct a tomographic image of an inspection object only when two detectors coincidentally detect two gamma rays generated by annihilation of positrons. Specifically, the inspection object is medicated with a radioactive drug including a positron-emitting radionuclide. The detectors, which include detector element groups constructed of numerous scintillators, for example, detect pair annihilation gamma rays of 511 keV released from the medicated inspection object. And when two detectors detect gamma rays within a certain period of time, it is regarded as a "coincident" detection, and is counted as a pair of pair annihilation gamma rays. Further, a generating position of the pair annihilation gamma rays is determined to be on a straight line linking the two detectors having detected them. Such coincidence information is accumulated and reconstruction processing is carried out to obtain a positron-emitting radionuclide distribution image, i.e. a tomographic image.

Such a PET apparatus generally is constructed by arranging a plurality of detectors in a circle to surround an inspection object for improvement in sensitivity. In the case of a site-specific PET apparatus for imaging parts of the inspection object such as the breasts, it is constructed to surround only the site to be imaged. Consequently, with a plurality of detectors arranged adjacent the site to be imaged, detection sensitivity can be further improved (see Japanese Unexamined Patent Publication No. 2009-30031, for example).

Figure 11:
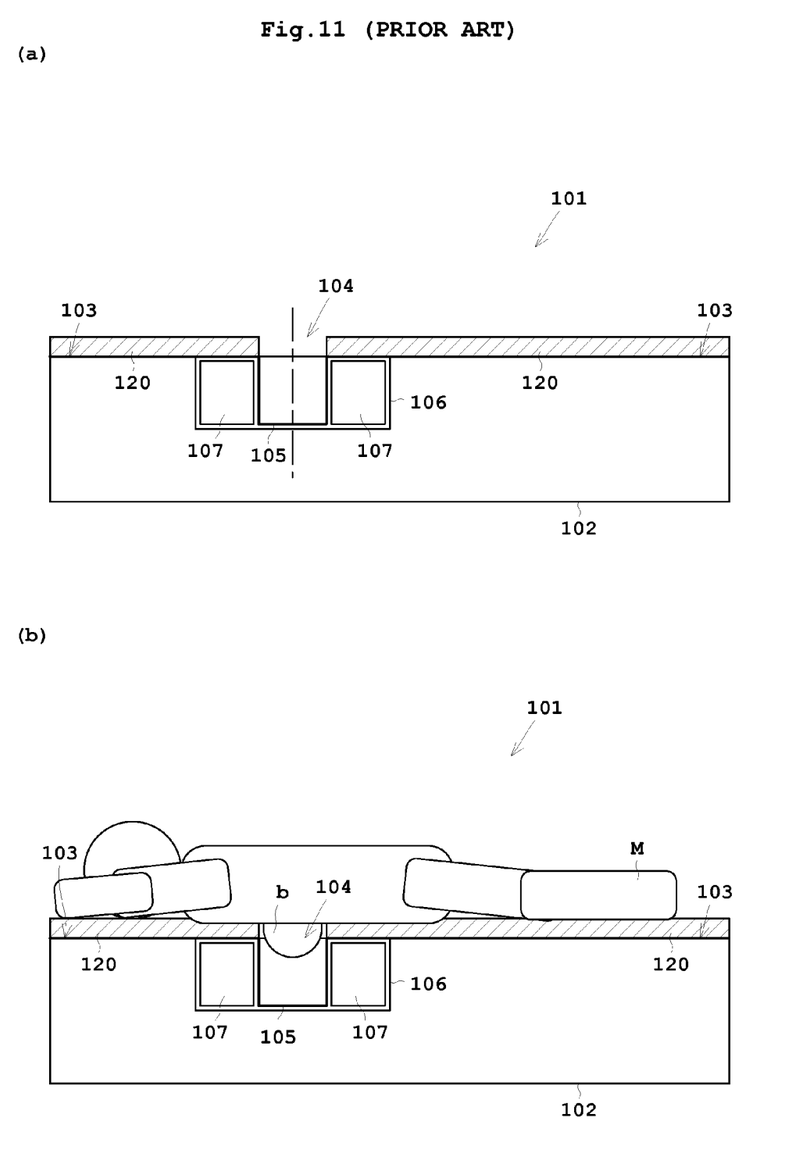

As shown in FIG. 11 (a) or FIG. 11 (b), a mammo-PET apparatus 101 for imaging the breasts of an inspection object has a support unit 102 on which the inspection object M is placed in a prone position (face-down state). A supporting surface 103 of the support unit 102 has an opening 104 formed therein to receive a breast b for diagnosing the breasts b below the supporting surface 103. A detector ring 106 is disposed inside the support unit 102 for detecting gamma rays generated from the inspection object M, the detector ring 106 (a plurality of gamma-ray detectors 107) being arranged to surround the breast b inserted in the opening 104. A mat 120 serving as a cushion is laid on the supporting surface 103 of the support unit 102 (see Japanese Unexamined Patent Publication No. 2008-232913, for example).

Figure 12:
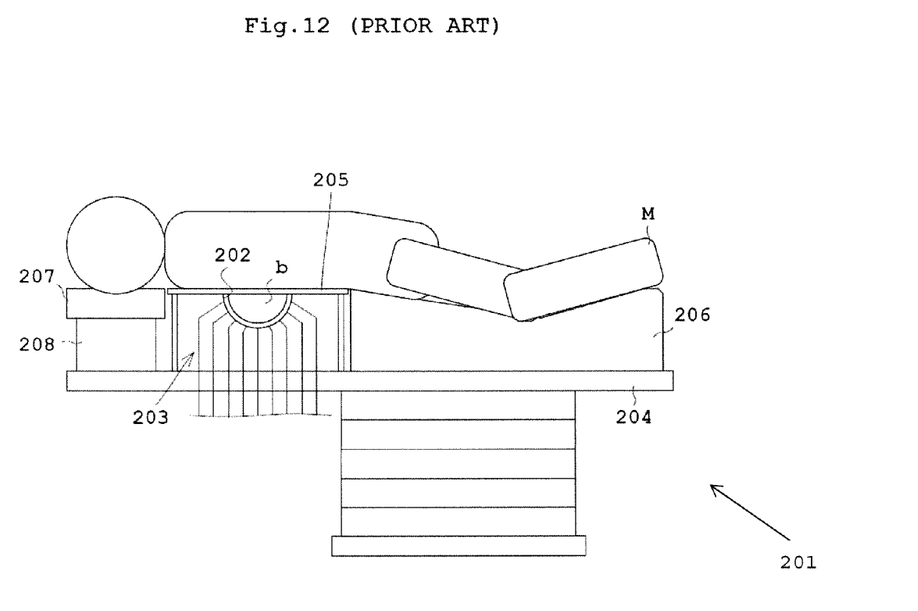
FIG. 12 is a side view showing a conventional apparatus.

There is the following as an apparatus which images the breasts of an inspection object (see Japanese Unexamined Patent Publication No. 2009-189726, for example). As shown in FIG. 12, this apparatus has a bed 201 for supporting an inspection object M in a prone position. This bed 201 has a hemispherical vessel 202 attached thereto for surrounding a breast b of the inspection object M, and a measuring unit 203 is provided for the vessel 202. Mounted on a base 204 of the bed 201 are a chest supporting plate 205, a mat 206 and a pillow 207. The chest supporting plate 205 is formed of a plate-like member for supporting the chest of the inspection object M. The mat 206 is formed of a soft material for supporting a portion from the abdomen to the legs of the inspection object M. A portion of an upper surface of the mat 206 which supports the knees of the inspection object M is lower than the other portions, to ease a burden when the inspection object M takes a position for a time of measurement. The pillow 207 supports the head of the inspection object M, is formed of a soft member, and is mounted on the base 204 through a height adjusting mechanism 208

[Patent Document 1]
Unexamined Patent Publication No. 2009-300319
[Patent Document 2]
Unexamined Patent Publication No. 2008-232913
[Patent Document 3]
Unexamined Patent Publication No. 2009-189726

SUMMARY OF INVENTION

Technical Problem

However, the conventional examples with such constructions have the following problems. With the apparatus 101 in which the breast b of the inspection object M inserted into the opening 104 formed in the supporting surface 103 of the support unit 102, i.e. into the field of view (detection range) of the detector ring 106, there is a problem that it is difficult to pick up images of the base portion of the breast b. Breast cancer often develops in the base portion of the breast b of the inspection object M, i.e. adjacent the chest wall of the inspection object M. Therefore, the breast b of the inspection object M must be inserted deeper into the field of view of the detector ring 106.

However, as shown in FIG. 11, the mat 120 as a cushion is laid on the support unit 102. In order to insert the breast b of the inspection object M deeper into the field of view of the detector ring 106, the chest of the inspection object M must be pressed toward the detector ring 106. It is conceivable, for example, to provide handles for pressing down with the inspection object's own force. Where, as shown in FIG. 12, the chest supporting plate 205 is not covered with a mat, a hard part will directly contact the inspection object M. For example, at a sternal part of the inspection object M, or a part of the inspection object M in contact with an outer edge of the vessel 202, considerable pain will be given to the inspection object M. With a PET apparatus which takes time for image pick-up, a slight posture change during image pick-up will have direct influence on the image quality of the images acquired.

This invention has been made having regard to the state of the art noted above, and its object is to provide a nuclear medicine diagnostic apparatus which enables an imaging site (breast) to be inserted deeper into a field of view of radiation detectors while reducing pain inflicted on an inspection object.

Solution to Problem

In order to fulfill the above object, this invention provides the following construction. A nuclear medicine diagnostic apparatus in this invention comprises a support unit for supporting an inspection object from front; an opening for receiving a breast of the inspection object supported by the support unit; radiation detectors opposed to the inspection object across a supporting surface of the support unit for detecting radiation generated from the breast; a first mat provided around the opening formed in the support unit for supporting the chest of the inspection object; and a second mat provided outward of the first mat for supporting the inspection object; wherein the first mat is formed of a material having a greater sagging rate than the second mat.

According to the nuclear medicine diagnostic apparatus in this invention, the inspection object is supported from front by the support unit, and a breast of the inspection object supported by the support unit is inserted into the opening. The support unit has the first mat and the second mat. The first mat is provided around the opening in the support unit for supporting the chest of the inspection object, and the second mat is provided outward of the first mat for supporting the inspection object. And the first mat is formed of a material having a greater sagging rate than the second mat.

The first mat is formed of a material having a greater sagging rate than the second mat. Therefore, when the inspection object is supported by the first mat and second mat, the first mat will sag deeper than the second mat. The first mat sagging deeper makes it easy to centralize the weight around the chest of the inspection object, i.e. the breast of the inspection object. Consequently, the inspection object can be pressed toward the radiation detectors naturally only by the weight of the inspection object. Therefore, the breast of the inspection object can be inserted deeper into the field of view of the radiation detectors. Since the chest of the inspection object is supported by the first mat, the load acting on the chest can be dispersed to ease the pain inflicted on the inspection object. Therefore, while easing the pain inflicted on the inspection object, the breast of the inspection object can be inserted deeper into the field of view of the radiation detectors.

Since the pain inflicted on the inspection object can be eased, it is easy to maintain the position of the inspection object. Therefore, body movement of the inspection object due to the pain received at the time of radiography can be inhibited, to improve the image quality of tomographic images acquired.

In the nuclear medicine diagnostic apparatus in this invention, one example of the first mat is constructed such that, when supporting the inspection object, part of the first mat reaches a limit of sagging. That is, when part of the first mat has reached the limit of sagging at the time of supporting the inspection object, the chest of the inspection object, i.e. the areas around the breast of the inspection object, is pressed, for example, due to the hardness of the supporting surface under the first mat. Consequently, the breast of the inspection object can be inserted deeper into the field of view of the radiation detectors.

In the nuclear medicine diagnostic apparatus in this invention, one example of the first mat is constructed such that, when supporting the inspection object, the first mat does not reach a limit of sagging. That is, when the first mat does not reach the limit of sagging at the time of supporting the inspection object, the first mat receives the chest of the inspection object in the state not sagging to the limit Since the weight is concentrated on the chest of the inspection object, the torso of the inspection object curves to a state of the chest naturally being stretched. Consequently, the breast of the inspection object can be inserted deeper into the field of view of the radiation detectors.

In the nuclear medicine diagnostic apparatus in this invention, it is preferable that the supporting surface of the support unit has an area corresponding to the head of the inspection object and recessed relative to an area corresponding to the chest of the inspection object. Since the head of the inspection object is a part structurally protruding forward of the chest wall, when pressing the inspection object toward the radiation detectors, load tends to be applied to the head, and this is obstructive to the pressing. However, the pain caused by the load applied to the head can be eased, and the inspection object can be pressed effectively toward the radiation detectors.

In the nuclear medicine diagnostic apparatus in this invention, it is preferable that the supporting surface of the support unit has an area corresponding to the arms of the inspection object and recessed relative to an area corresponding to the chest of the inspection object. Since the arms such as the shoulder bones of the inspection object are parts structurally protruding forward of the chest wall, when pressing the inspection object toward the radiation detectors, load tends to be applied to the arms, and this is obstructive to the pressing. However, the pain caused by the load applied to the arms can be eased, and the inspection object can be pressed effectively toward the radiation detectors.

In the nuclear medicine diagnostic apparatus in this invention, it is preferable that the supporting surface of the support unit is even in an area corresponding to the legs of the inspection object and an area corresponding to the chest of the inspection object. When the legs of the inspection object supported by the first mat and second mat sink deep, the inspection object will incline. Therefore, the load balance around the breast of the inspection object supported by the first mat will give way. In this case, pain may be given to the inspection object by outer edges of the opening contacting lower parts of the breast of the inspection object. So the supporting surface of the support unit being even in the area corresponding to the legs of the inspection object and the area corresponding to the chest of the inspection object can maintain the load balance. Therefore, while easing the pain inflicted on the inspection object, the breast of the inspection object can be inserted deeper into the field of view of the radiation detectors.

One example of the second mat of the nuclear medicine diagnostic apparatus in this invention is thicker in an area corresponding to the head of the inspection object than in an area corresponding to the abdomen of the inspection object. When the inspection object is supported by the first mat and second mat, the inspection object may incline toward the head, depending on the inspection object. By making the second mat thicker in the area corresponding to the head of the inspection object than in the area corresponding to the abdomen of the inspection object, the load balance around the breast of the inspection object supported by the first mat can be adjusted.

One example of the second mat of the nuclear medicine diagnostic apparatus in this invention is thicker in an area corresponding to the legs of the inspection object than in an area corresponding to the abdomen of the inspection object. When the inspection object is supported by the first mat and second mat, the inspection object may incline toward the legs, depending on the inspection object. By making the second mat thicker in the area corresponding to the legs of the inspection object than in the area corresponding to the abdomen of the inspection object, the load balance around the breast of the inspection object supported by the first mat can be adjusted.

One example of the nuclear medicine diagnostic apparatus in this invention has a detector ring having a plurality of detectors arranged in a ring form. This enables the breast of the inspection object to be imaged with high sensitivity.

One example of the first mat of the nuclear medicine diagnostic apparatus in this invention is provided in an area corresponding to the detector ring around the opening formed in the support unit. Since the first mat is formed circular, it is easy to adjust a load balance applied around the opening.

Advantageous Effects of Invention

According to the nuclear medicine diagnostic apparatus in this invention, the first mat is formed of a material having a greater sagging rate than the second mat. Therefore, when the inspection object is supported by the first mat and second mat, the first mat will sag deeper than the second mat. The first mat sagging deeper makes it easy to centralize the weight around the chest of the inspection object, i.e. the breast of the inspection object. Consequently, the inspection object can be pressed toward the radiation detectors naturally only by the weight of the inspection object. Therefore, the breast of the inspection object can be inserted deeper into the field of view of the radiation detectors. Since the chest of the inspection object is supported by the first mat, the load acting on the chest can be dispersed to ease the pain inflicted on the inspection object. Therefore, while easing the pain inflicted on the inspection object, the breast of the inspection object can be inserted deeper into the field of view of the radiation detectors.

Since the pain inflicted on the inspection object can be eased, it is easy to maintain the position of the inspection object. Therefore, body movement of the inspection object due to the pain received at the time of radiography can be inhibited, to improve the image quality of tomographic images acquired.

BRIEF DESCRIPTION OF DRAWINGS

FIG. 1(a) is a side view showing a mammo-PET apparatus in Embodiment 1, and (b) is a side view showing the mammo-PET apparatus of (a) in a state of supporting an inspection object;

FIG. 5(a) is a side view showing the mammo-PET apparatus in Embodiment 2, and (b) is a side view showing the mammo-PET apparatus of (a) in a state of supporting an inspection object;

FIG. 6(a) is a side view showing a mammo-PET apparatus in Embodiment 3, and (b) is a side view showing the mammo-PET apparatus of (a) in a state of supporting an inspection object;

FIG. 7(a) is a side view showing a modified mammo-PET apparatus, and (b) is a side view showing the mammo-PET apparatus of (a) in a state of supporting an inspection object;

FIGS. 9(a) and (b) are views showing modified radiation detectors;

FIG. 11(a) is a side view showing a conventional mammo-PET apparatus, (b) is a side view showing the mammo-PET apparatus of (a) in a state of supporting an inspection object.

DESCRIPTION OF EMBODIMENTS

Embodiment 1

Figure 2:
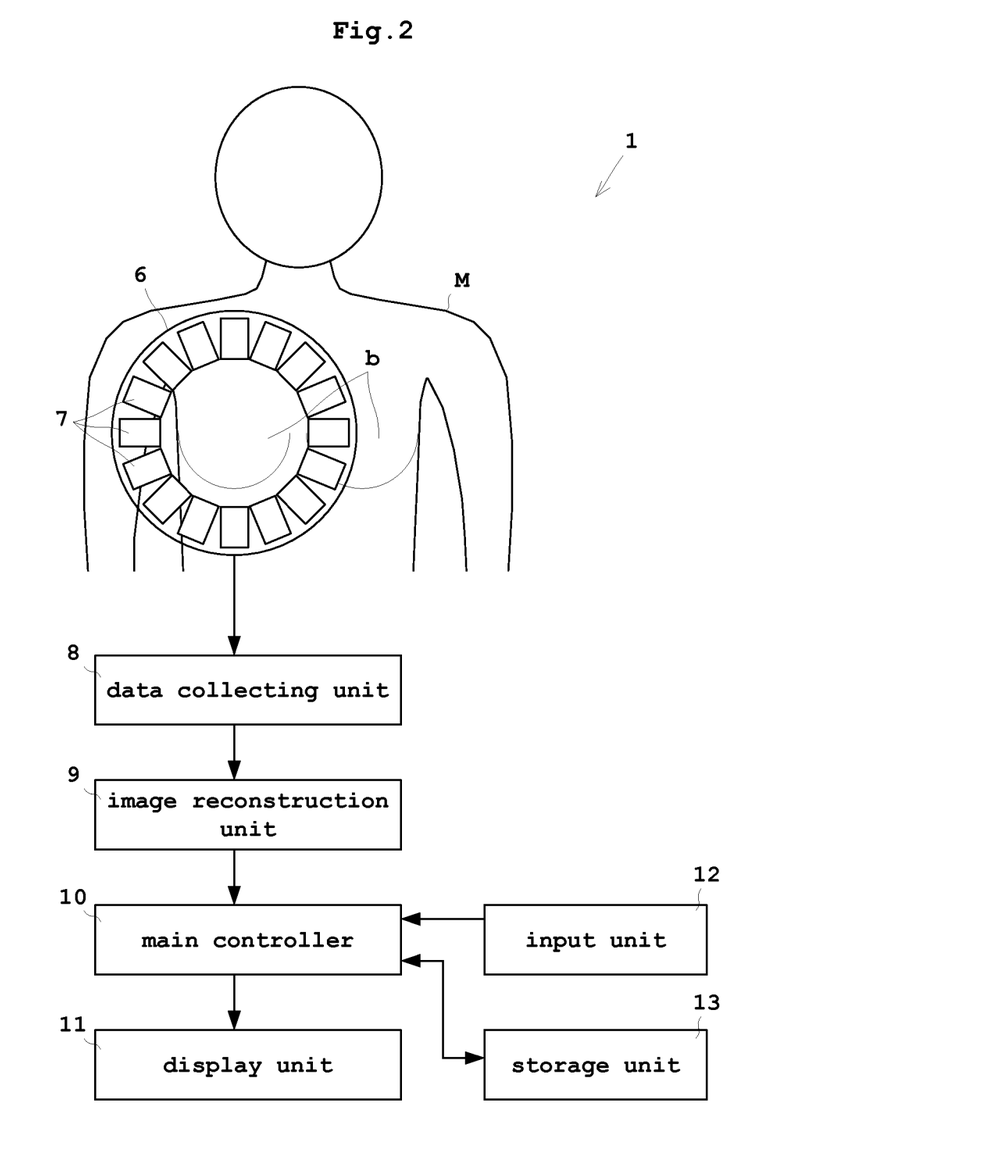
FIG. 2 is a block diagram showing the mammo-PET apparatus in Embodiment 1.
Figure 3:
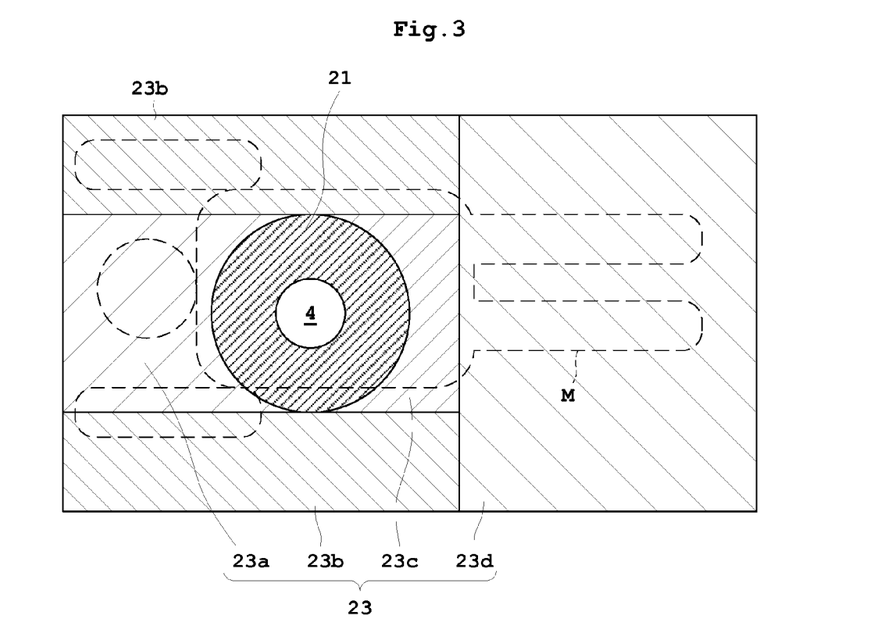
FIG. 3 is a view for use in description of a chest mat and an outer mat.

Embodiment 1 of this invention will be described hereinafter with reference to the drawings. FIG. 1(a) is a side view showing a mammo-PET apparatus in Embodiment 1. FIG. 1(b) is a side view showing the mammo-PET apparatus of FIG. 1(a) in a state of supporting an inspection object. FIG. 2 is a block diagram showing the mammo-PET apparatus. FIG. 3 is a view for use in description of a chest mat and an outer mat. The mammo-PET apparatus will be described as an example of nuclear medicine diagnostic apparatus.

Reference is made to FIG. 1(a) or FIG. 1(b). A mammo-PET apparatus 1 includes a support unit 2 (or also called a gantry) for supporting an inspection object M from front. The inspection object M is supported in a prone position by the support unit 2. The support unit 2 has an opening 4 formed in a support surface 3 thereof for receiving a breast b of the inspection object M supported by the support unit 2. The opening 4 has a receptacle 5 which receives the breast b of the inspection object M. In this embodiment, the support unit 2 is constructed so that the support surface 3 will be horizontal.

A detector ring 6 is mounted in the support unit 2 for detecting gamma rays generated from the breast b of the inspection object M. The detector ring 6 is disposed opposite the inspection object M across the supporting surface 3 of the support unit 2. The detector ring 6 is constructed of a plurality of gamma-ray detectors 7 arranged in a ring form including a polygonal shape about an axis 6a extending perpendicular to the supporting surface 3 and through the receptacle 5 (FIG. 2). The detector ring 6 corresponds to the radiation detectors in this invention. The gamma-ray detectors 7 correspond to the detectors in this invention.

The gamma-ray detectors 7 have scintillator blocks, light guides and photomultiplier tubes (none of them being shown). A scintillator block is constructed of a plurality of scintillators. Gamma rays generated from the breast b of the inspection object M medicated with a radioactive drug are converted into light by the scintillator blocks. The converted light is guided by the light guides to the photomultiplier tubes. The photomultiplier tubes carry out photoelectric conversion and output electric signals. As the gamma-ray detectors 7, DOI (depth of interaction) detectors are used which are constructed of scintillator blocks in multiple layers, for example, and which can acquire position information in depth directions.

As shown in FIG. 2, a data collecting unit 8 is connected to the detector ring 6 (gamma-ray detectors 7). The data collecting unit 8 collects an event as coincidence counting information only when two gamma-ray detectors 7 detect a gamma ray pair within a fixed period. An image reconstruction unit 9 accumulates coincidence counting information, and carries out image reconstruction processing of the accumulated coincidence counting information to generate tomographic images (positron-emitting radionuclide distribution images).

The mammo-PET apparatus 1 includes a main controller 10 for performing overall control of the respective components of this apparatus 1, a display unit 11 for displaying the tomographic images generated by the image reconstruction unit 9, an input unit 12 for the operator to make input settings and various controls, and a storage unit 13 for storing the tomographic images generated by the image reconstruction unit 9, for example. The main controller 10 is formed of a central processing unit (CPU) and the like. The display unit 11 is formed of a monitor, for example. The input unit 12 includes a keyboard, a mouse and so on. The storage unit 13 is formed of storage media such as a ROM (Read-only Memory), RAM (Random-Access Memory) or hard disk.

Figure 1:
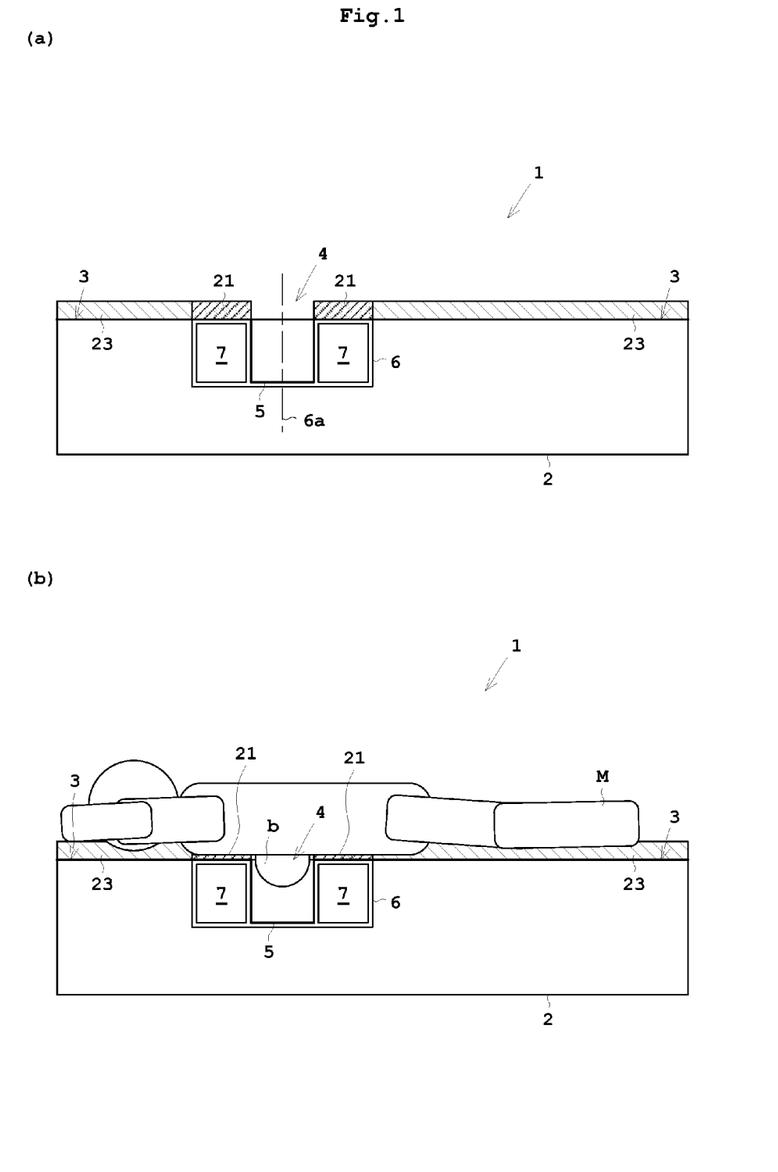

Reference is made back to FIG. 1(*a*) or FIG. 1(*b*). The mammo-PET apparatus 1 includes a chest mat (also called a cushion or mattress) 21 formed around the opening 4 in the support unit 2, and an outer mat 23 formed outward of the chest mat 21 on the support unit 2. The chest mat 21 is formed circular along outer edges of the detector ring 6. The chest mat 21 supports areas around the breast b of the inspection object M, i.e. the chest of the inspection object M, inserted into the opening 4. The outer mat 23 supports portions of the inspection objects M other than the areas around the breast b supported by the chest mat 21, i.e. portions other than the chest of the inspection object M. The chest mat 21 is formed of a material having a greater sagging rate (compression rate) than the outer mat 23.

The chest mat 21 is formed of an elastic material such as sponge, for example. When the chest mat 21 supports the inspection object M, it will be squeezed thin and the areas around the breast b will be pressed by the rigidity of the supporting surface 3 present underneath. That is, the chest mat 21 is constructed to have part of the chest mat 21 reach a limit of sagging when supporting the inspection object M. The chest mat 21 is constructed 1 cm thick, for example, and is squeezable as thin as 1 mm thick. The chest mat 21 has a predetermined thickness when not supporting the inspection object M, to be squeezable while adjusting the balance of load (while distributing load) acting on the areas around the breast b of the inspection object M.

The outer mat 23 is formed of an elastic material such as low rebounding urethane, for example. The outer mat 23 receives the inspection object M softly. When supporting the inspection object M, the outer mat 23 will sag according to the shape of the inspection object M. The outer mat 23 is constructed 4 cm thick, for example.

As shown in FIG. 3, the outer mat 23 includes an area 23*a* corresponding to the head of the inspection object M, areas 23*b* corresponding to the sides, i.e. the arms of the inspection object M, an area 23*c* corresponding to the abdomen of the inspection object M, and an area 23*d* corresponding to the legs of the inspection object M. The outer mat 23 is formed to have the same thickness in the areas 23*a*-23*d*.

The chest mat 21 may be formed to spread outward of an area corresponding to the detector ring 6 (i.e. of the outer edge of the detector ring 6), or to remain inward thereof. The outer edge of the chest mat 21 may be shaped circular to receive load equally, or may be shaped polygonal. The chest mat 21 corresponds to the first mat in this invention. The outer mat 23 corresponds to the second mat in this invention.

Next, operation of the mammo-PET apparatus 1 in Embodiment 1 will be described. FIG. 1(*a*) shows a state where the inspection object M is not supported by the chest mat 21 and outer mat 23. The inspection object M is placed in a prone position on the chest mat 21 and outer mat 23 (support unit 2). At this time, the breast b of the inspection object M is inserted into the opening 4. When the inspection object M is placed, the chest mat 21 and outer mat 23 will sag under the weight of the inspection object M (FIG. 1(*b*)). Since the chest mat 21 is formed of a material having a greater sagging rate (compression rate) than the outer mat 23, the chest mat 21 sags deeper than the outer mat 23 when the same load is applied. This makes it easy to centralize weight on the chest of the inspection object M, i.e. areas around the breast b of the inspection object M, supported by the chest mat 21. This makes a state of pressing the inspection object M toward the detector ring 6 only with the weight of the inspection object M.

And when the inspection object M is pressed toward the detector ring 6 only with the weight of the inspection object M, the chest mat 21 will have part of the chest mat 21 reach the limit of sagging at the time of supporting the inspection object M. That is, the chest mat 21 which is 1 cm thick is squeezed as thin as 1 mm thick, for example. With the squeeze to 1 mm thickness, the hardness of the supporting surface 3 underneath will produce a state of pressing the chest of the inspection object M, i.e. the areas around the breast b of the inspection object M. Consequently, the breast b of the inspection object M is inserted deeper into the field of view of the detector ring 6. Since the load balance around the breast b of the inspection object M is adjusted by the elasticity of the chest mat 21, the pain inflicted on the inspection object M is eased. Therefore, the breast b of the inspection object M is inserted deeper into the field of view of the detector ring 6 while easing the pain inflicted on the inspection object M with the elasticity of the chest mat 21. So the breast b, including the base portion thereof, is inserted into the field of view of the detector ring 6.

Thus, image pickup (inspection) is carried out with the inspection object M lying in a prone position on the chest mat 21 and outer mat 23 and with the breast b, including the base portion, inserted deep into the field of view of the detector ring 6. The inspection object M is medicated with a radioactive drug beforehand. Consequently, gamma rays are generated from the breast b of the inspection object M. A pair of gamma rays generated are emitted in 180° opposite directions. The gamma-ray detectors 7 of the detector ring 6 detect the pair of gamma rays. The data collecting unit 8 collects, as coincidence counting information, events in which a gamma ray pair is detected by two gamma-ray detectors 7 within a fixed period. The image reconstruction unit 9 accumulates the coincidence counting information, and carries out reconstruction processing of the accumulated coincidence counting information to generate tomographic images. The generated tomographic images are displayed on the display unit 11, and are stored in the storage unit 13.

According to the mammo-PET apparatus 1 in Embodiment 1, the inspection object M is supported by the support unit 2 from front, and the breast b of the inspection object M supported by the support unit 2 is inserted into the opening 4. The support unit 2 has the chest mat 21 and outer mat 23. The chest mat 21 is formed around the opening in the support unit for supporting the chest of the inspection object. The outer mat 23 is formed outward of the chest mat 21 for supporting the inspection object. And the chest mat 21 is formed of a material having a greater sagging rate than the outer mat 23.

The chest mat 21 is formed of a material having a greater sagging rate than the outer mat 23. Therefore, when the inspection object M is supported by the chest mat 21 and outer mat 23, the chest mat 21 will sag deeper than the outer mat 23. The chest mat 21 sagging deeper makes it easy to centralize the weight around the chest of the inspection object M, i.e. the breast b of the inspection object M. Consequently, the inspection object M can be pressed toward the detector ring 6 naturally only by the weight of the inspection object M. Therefore, the breast b of the inspection object M can be inserted deeper into the field of view of the detector ring 6. Since the chest of the inspection object M is supported by the chest mat 21, the load acting on the chest can be dispersed to ease the pain inflicted on the inspection object M. Therefore, while easing the pain inflicted on the inspection object M, the breast of the inspection object can be inserted deeper into the field of view of the radiation detectors.

Since the pain inflicted on the inspection object M can be eased, it is easy to maintain the position of the inspection object M. Therefore, body movement of the inspection object M due to the pain received at the time of radiography can be inhibited, to improve the image quality of tomographic images acquired.

When part of the chest mat 21 has reached the limit of sagging at the time of supporting the inspection object M, the chest of the inspection object M, i.e. the areas around the breast b of the inspection object M, is pressed, for example, due to the hardness of the supporting surface 3 under the chest mat 21. Consequently, the breast b of the inspection object M can be inserted deeper into the field of view of the detector ring 6.

Since the detector ring 6 having a plurality of gamma-ray detectors 7 arranged in a ring form is used, the breast of the inspection object can be imaged with high sensitivity. The chest mat 21 is formed in an area corresponding to the detector ring 6 around the opening 4 in the support unit 2. Since the chest mat 21 is formed circular, it is easy to adjust a load balance applied around the opening 4.

Embodiment 2

Figure 4:
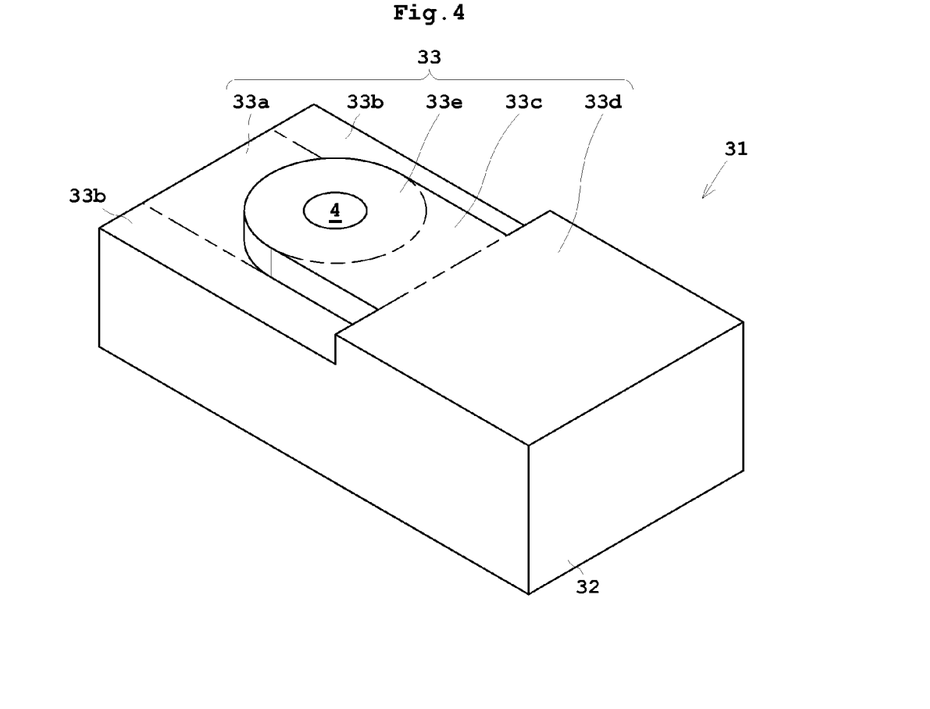
FIG. 4 is a perspective view showing a support unit of a mammo-PET apparatus in Embodiment 2.
Figure 5:
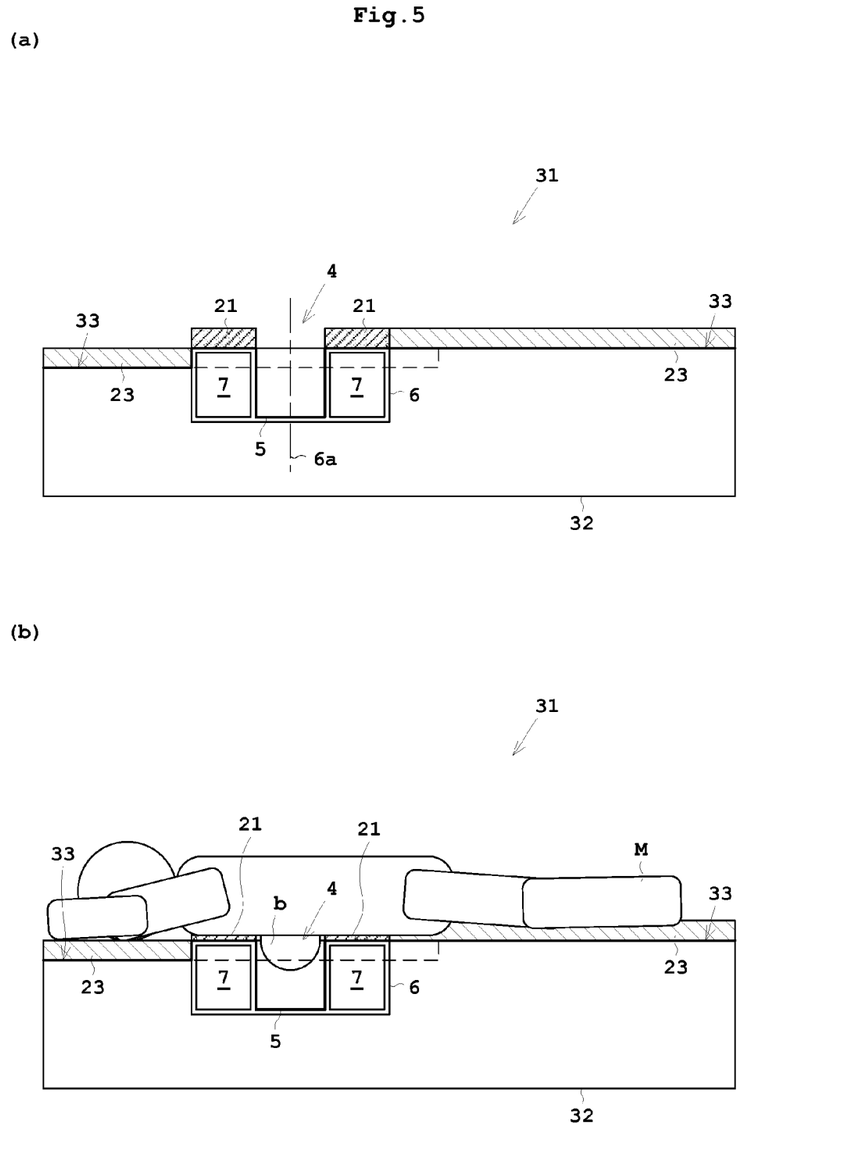

Embodiment 2 of this invention will be described hereinafter with reference to the drawings. FIG. 4 is a perspective view showing a support unit of a mammo-PET apparatus in Embodiment 2. FIG. 5(a) is a side view showing the mammo-PET apparatus in Embodiment 2, and FIG. 5(b) is a side view showing the mammo-PET apparatus of FIG. 5(a) in a state of supporting an inspection object. Components overlapping those in foregoing Embodiment 1 will not be described.

Reference is made to FIG. 4. The support unit 32 of the mammo-PET apparatus 31 in Embodiment 2 has a level difference on a supporting surface 33 thereof. The supporting surface 33 of the support unit 32 includes an area 33a corresponding to the head of the inspection object M, areas 33b corresponding to the sides, i.e. the arms, of the inspection object M, an area 33c corresponding to the abdomen of the inspection object M, an area 33d corresponding to the legs of the inspection object M, and an area 33e corresponding to the chest of the inspection object M.

The supporting surface 33 of the support unit 32 has the area 33a corresponding to the head of the inspection object M and the areas 33b corresponding to the arms of the inspection object M which are recessed relative to the area 33e corresponding to the chest of the inspection object. That is, the supporting surface 33 in the areas 33a and 33b corresponding to the head and the arms is formed in positions one level lower than the chest area 33e (e.g. by about 4 cm). Further, the supporting surface 33 of the support unit 32 is even in the area 33c corresponding to the abdomen of the inspection object M, the area 33d corresponding to the legs of the inspection object M and the area 33e corresponding to the chest of the inspection object M.

As shown in FIG. 5(a), the chest mat 21 and outer mat 23 are formed on the support unit 32 of the mammo-PET apparatus 31. The inspection object M is placed as shown in FIG. 5(b).

According to the mammo-PET apparatus 31 in Embodiment 2, the supporting surface 33 of the support unit 32 has the area 33a, 33b corresponding to at least one of the head and the arms of the inspection object M recessed relative to the area 33e corresponding to the chest of the inspection object M. The head and the arms such as the shoulder bones of the inspection object are parts structurally protruding forward of the chest wall. Therefore, when pressing the inspection object M toward the detector ring 6, load tends to be applied to the head and arms, and this is obstructive to the pressing although the load is lightened by the outer mat 23. However, the pain caused by the load applied to the head and arms can be eased, and the inspection object M can be pressed effectively toward the detector ring 6.

When the legs of the inspection object M supported by the chest mat 21 and outer mat 23 sink deep, the inspection object M will incline. Therefore, the load balance around the breast b of the inspection object M supported by the chest mat 21 will give way. In this case, pain may be given to the inspection object by outer edges of the opening 4 contacting lower parts of the breast b of the inspection object M, or with the load tending to act on the knees of the inspection object M. So the supporting surface 33 of the support unit 32 being even in the area 33d corresponding to the legs of the inspection object M and the area 33e corresponding to the chest of the inspection object can maintain the load balance. Therefore, while easing the pain inflicted on the inspection object M, the breast b of the inspection object M can be inserted deeper into the field of view of the detector ring 6.

Embodiment 3

Figure 6:
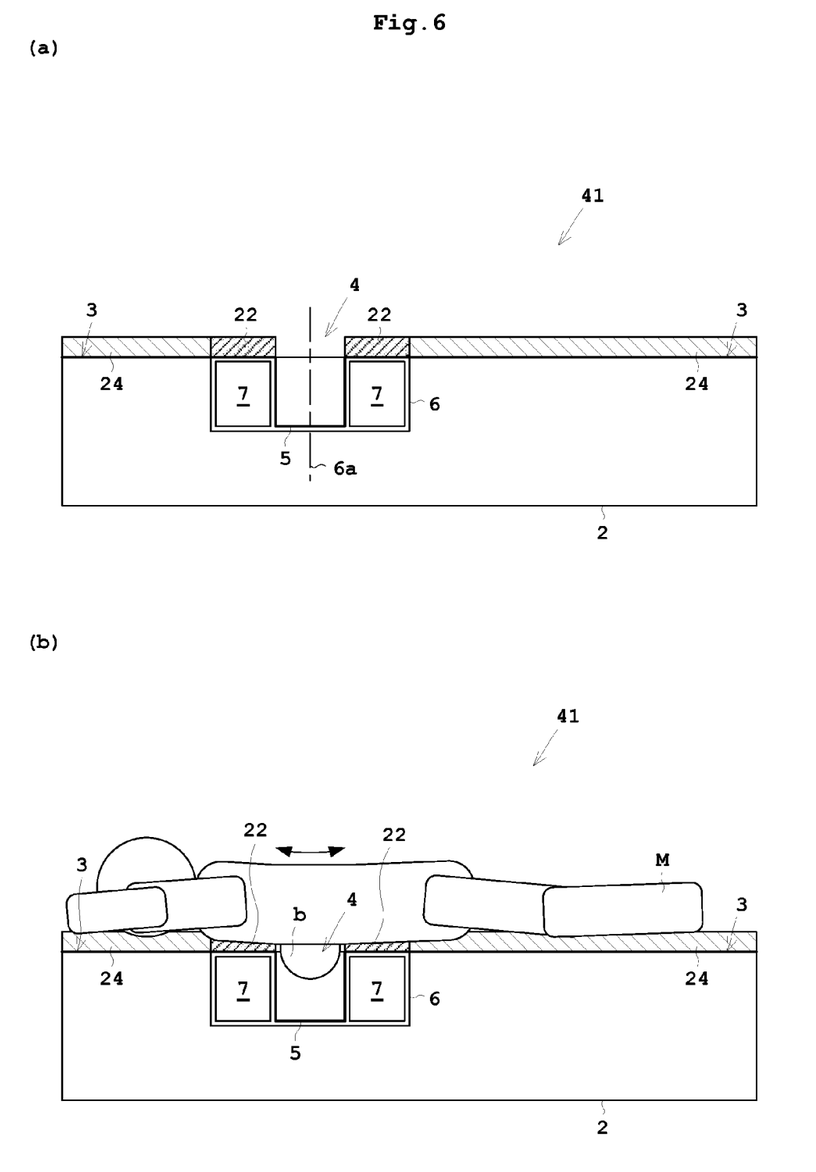

Embodiment 3 of this invention will be described hereinafter with reference to the drawings. FIG. 6(a) is a side view showing a mammo-PET apparatus in Embodiment 3, and FIG. 6(b) is a side view showing the mammo-PET apparatus of FIG. 6(a) in a state of supporting an inspection object. Components overlapping those in foregoing Embodiment 1 will not be described.

In Embodiment 1, the chest mat 21 of the mammo-PET apparatus 1 is constructed to have part of the chest mat 21 reach the limit of sagging when supporting the inspection object M. However, as shown in FIG. 6(b), the chest mat 22 of the mammo-PET apparatus 41 may be constructed not to have part of the chest mat 22 reach the limit of sagging when supporting the inspection object M. This construction is realized, for example, by changing the sagging rate (compression rate) of the chest mat 22 or the outer mat 24. The chest mat 22 corresponds to the first mat in this invention. The outer mat 24 corresponds to the second mat in this invention.

FIG. 6(a) shows a state where the inspection object M is not supported by the chest mat 22 and outer mat 24. When the inspection object M is placed, the chest mat 22 and outer mat 24 will sag under the weight of the inspection object M (FIG. 6(b)). Since the chest mat 22 is formed of a material having a greater sagging rate (compression rate) than the outer mat 24, the chest mat 22 sags deeper than the outer mat 24 when the same load is applied. This makes it easy to centralize weight on the chest of the inspection object M, i.e. areas around the breast b of the inspection object M, supported by the chest mat 22. This makes a state of pressing the inspection object M toward the detector ring 6 only with the weight of the inspection object M. And the chest mat 22 is constructed such that, at the time of supporting the inspection object M, the chest mat 22 will not reach the limit of sagging. Therefore, the inspection object M will take a position having her chest out as shown in FIG. 6(b). Even if peripheries of the breast contact edges of the opening 4, load will be dispersed by the elasticity of the chest mat 21, thereby to ease the pain.

According to the mammo-PET apparatus 41 in Embodiment 3, with the chest mat 22 not reaching the limit of sagging at the time of supporting the inspection object M, the chest mat 22 receives the chest of the inspection object M in the state not sagging to the limit. Since the weight is concentrated on the chest of the inspection object M, the torso of the inspection object M curves to a state of the chest naturally being stretched. Consequently, the breast b of the inspection object M can be inserted deeper into the field of view of the detector ring 6.

This invention is not limited to the foregoing embodiments, but may be modified as follows:

(1) In Embodiment 1 and Embodiment 2 described above, the outer mat 23 has a uniform thickness. In a mammo-PET apparatus 51, the outer mat 23 may have thickness adjustable in at least one of the areas 23a and 23d (FIG. 3) corresponding to the head and the legs of the inspection object M. That is, in the mammo-PET apparatus 51, the outer mat 23 is formed to have a larger thickness in at least one of the areas 23a and 23d corresponding to the head and the legs of the inspection object than the thickness of the areas 23b and 23c corresponding to the arms or the abdomen of the inspection object M.

Figure 7:
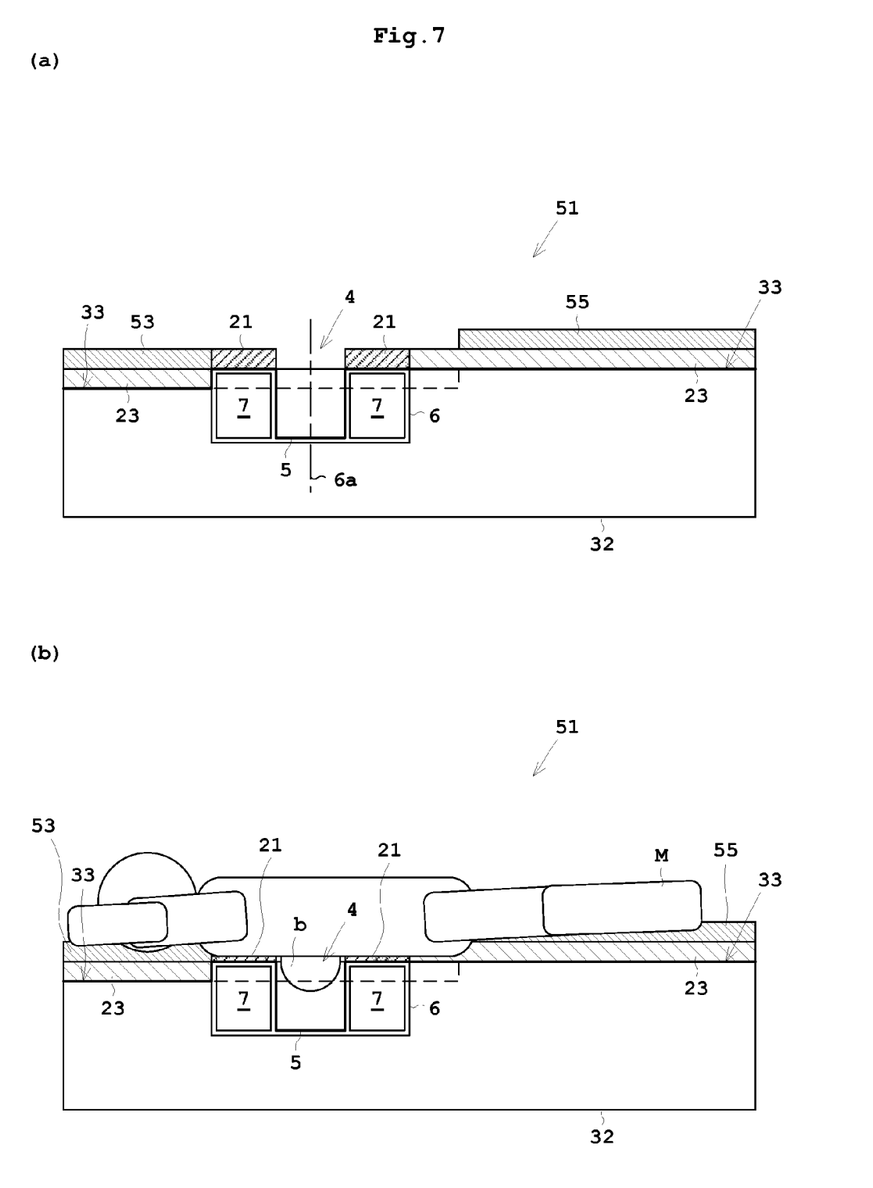

Reference is made to FIG. 7. In the mammo-PET apparatus 51, for example, an additional head mat 53 is formed in the area 23a (FIG. 3) of the outer mat 23 corresponding to the head of the inspection object M, and an additional leg mat 55 is formed in the area 23d (FIG. 3) of the outer mat 23 corresponding to the legs of the inspection object M.

When the inspection object M is supported by the chest mat 21 and outer mat 23, the inspection object M may incline toward the head or legs, depending on the inspection object M. Therefore, for example, the load balance around the breast b of the inspection object M supported by the chest mat 21 will give way. In this case, pain may be given to the inspection object by outer edges of the opening 4 contacting upper or lower parts of the breast b of the inspection object M. So, by adding the head mat 53 or leg mat 55, for example, to form the outer mat 23 having a larger thickness in at least one of the areas 23a and 23d corresponding to the head and the legs of the inspection object M than the thickness of the areas 23b and 23c corresponding to the arms or the abdomen of the inspection object M, the load balance around the breast b of the inspection object M supported by the chest mat 21 can be adjusted.

Figure 8:
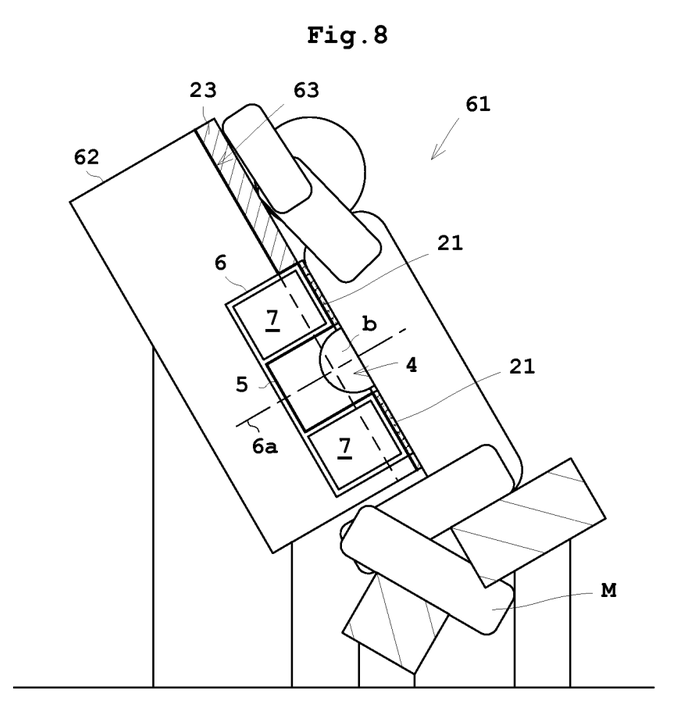
FIG. 8 is a side view showing a modified mammo-PET apparatus.

(2) In each embodiment and the modification described above, the supporting surface 3, 33 of the support unit 2, 32 is horizontal. As shown in FIG. 8, a mammo-PET apparatus 61 may have a construction in which the inspection object M seated on a chair (seated position) leans against the detector ring 6. In this case, a supporting surface 63 of a support block 62 is disposed at an angle, and the detector ring 6 is perpendicular to the supporting surface 63 and has a plurality of gamma-ray detectors 7 arranged in a ring form including a polygonal shape about the axis 6a of the receptacle 5.

Figure 9:
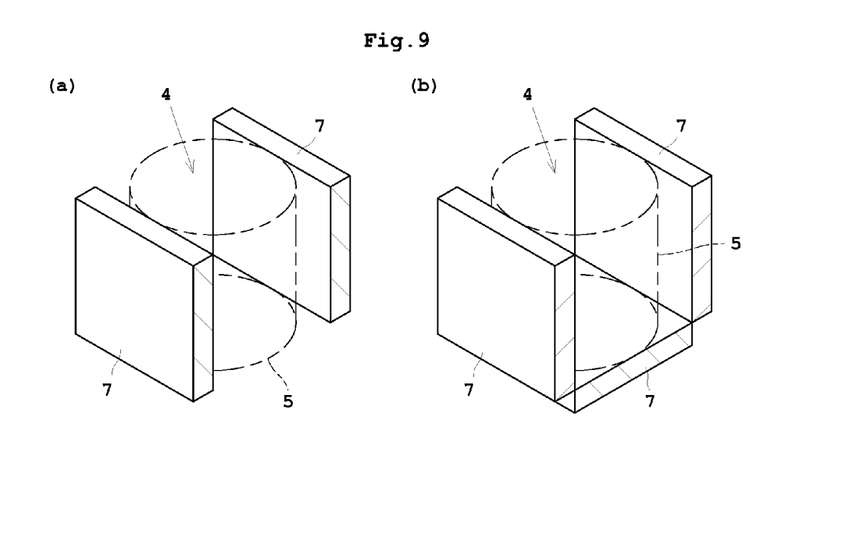

(3) In each embodiment or each modification described above, the mammo-PET apparatus 1, 31, 41, 51, 61 uses the detector ring 6 as radiation detectors, but this is not limitative. As shown in FIG. 9(a), for example, the receptacle 5 may be constructed to receive the breast b of the inspection object M in a position between two gamma-ray detectors 7. As shown in FIG. 9(b), the receptacle 5 may be constructed to receive the breast b of the inspection object M as enclosed from three directions by three gamma-ray detectors 7.

Figure 10:
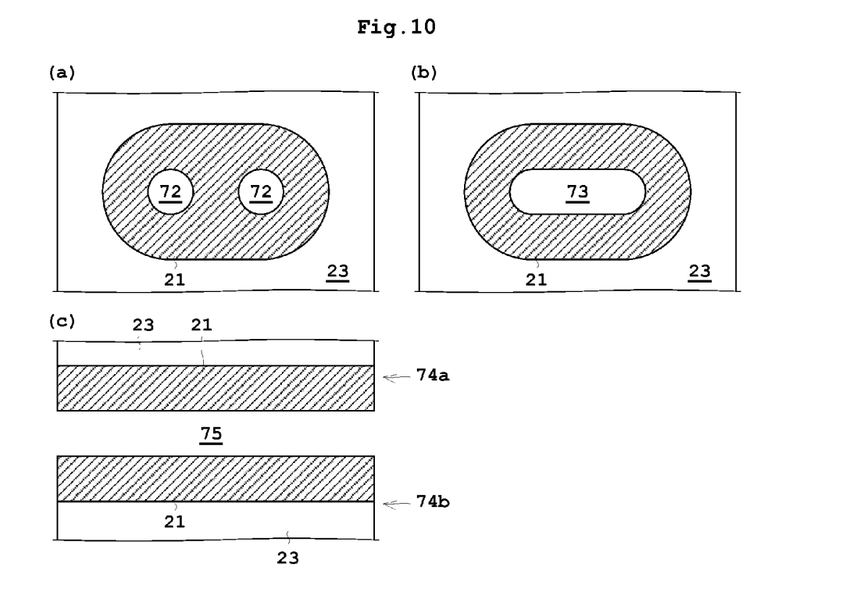
FIGS. 10(a)-(c) are plan views showing modified openings.

(4) In each embodiment or each modification described above, the opening 4 receives one breast b of the inspection object M, but this is not limitative. As shown in FIG. 10(a), for example, two openings 72 may be formed in the supporting surface of the support unit. As shown in FIG. 10(b), one opening 73 may be provided for receiving the two breasts b of the inspection object M. As shown in FIG. 10(c), an opening 75 may be provided by separated supporting surfaces 74a and 74b. The chest mat 21 (22) is formed around each opening 72, 73 and 75, and the outer mat 23 (24) is formed outward of the chest mat 21.

(5) In each embodiment or each modification described above, the chest mat 21 (22) is formed of sponge, and the outer mat 23 (24) is in form of a low rebounding mat, but this is not limitative. For example, the outer mat 23 may be formed of low rebounding urethane, and the chest mat 21 may be formed of low rebounding urethane softer (with a greater sagging rate) than the outer mat 23.

(6) In each embodiment or each modification described above, the outer mat 23 is formed entirely of low rebounding urethane, but this is not limitative. For example, in order to adjust the load balance around the breast b of the inspection object M supported by the chest mat 21, the material of the outer mat may be varied for each of the areas corresponding to the head, arms, abdomen and legs of the inspection object M.

(7) In each embodiment or each modification described above, the mammo-PET apparatus for imaging the breasts b of the inspection object M has been described as a nuclear medicine diagnostic apparatus. However, other sites may be imaged.

The invention claimed is:

1. A nuclear medicine diagnostic apparatus comprising:
a support unit for supporting an inspection object at one side of a supporting surface of the support unit, the support unit having an opening for receiving a breast of the inspection object;
a radiation detector disposed on another side of the supporting surface, the other side being an opposite side to the one side of the supporting surface, for detecting radiation generated from the breast;
a first mat provided on the one side of the supporting surface around the opening for supporting a chest of the inspection object; and
a second mat provided on the one side of the supporting surface outward of the first mat for supporting the inspection object,
wherein the first mat includes a material having a greater compression rate than the second mat.

2. The nuclear medicine diagnostic apparatus according to claim 1, wherein the supporting surface of the support unit has an area configured for supporting a head of the inspection object and recessed relative to an area which is configured for supporting the chest of the inspection object.

3. The nuclear medicine diagnostic apparatus according to claim 1, wherein the supporting surface of the support unit has an area configured for supporting arms of the inspection object and recessed relative to an area which is configured for supporting the chest of the inspection object.

4. The nuclear medicine diagnostic apparatus according to claim 1, wherein the supporting surface of the support unit is even in an area configured for supporting legs of the inspection object and an area configured for supporting the chest of the inspection object.

5. The nuclear medicine diagnostic apparatus according to claim 1, wherein the second mat is thicker in an area configured for supporting a head of the inspection object than in an area configured for supporting an abdomen of the inspection object.

6. The nuclear medicine diagnostic apparatus according to claim 1, wherein the second mat is thicker in an area configured for supporting legs of the inspection object than in an area configured for supporting an abdomen of the inspection object.

7. The nuclear medicine diagnostic apparatus according to claim 1, wherein the radiation detector is a detector ring having a plurality of detectors arranged in a circumferential direction.

8. The nuclear medicine diagnostic apparatus according to claim 7, wherein the first mat is provided in an area corresponding to the detector ring around the opening.

9. The nuclear medicine diagnostic apparatus according to claim 1, wherein the first mat is provided in the one side of the supporting surface immediately around the opening at the support unit.

* * * * *